United States Patent
Richardson et al.

(10) Patent No.: US 6,753,308 B1
(45) Date of Patent: Jun. 22, 2004

(54) REDUCTION OF MALODOUR

(75) Inventors: Anne Richardson, Kent (GB); John Martin Behan, Kent (GB); Emma Mason, Bedford (GB)

(73) Assignee: Quest International B.V., Naarden (NL)

( * ) Notice: Subject to any disclaimer, the term of this patent is extended or adjusted under 35 U.S.C. 154(b) by 0 days.

(21) Appl. No.: 09/868,594

(22) PCT Filed: Dec. 16, 1999

(86) PCT No.: PCT/GB99/04278

§ 371 (c)(1),
(2), (4) Date: Sep. 21, 2001

(87) PCT Pub. No.: WO00/37117

PCT Pub. Date: Jun. 29, 2000

(30) Foreign Application Priority Data

Dec. 22, 1998 (EP) .............................. 98310619

(51) Int. Cl.[7] ................................. A61K 7/46
(52) U.S. Cl. ................... 512/1; 424/4; 424/5
(58) Field of Search .............................. 512/1; 424/4, 5

(56) References Cited

U.S. PATENT DOCUMENTS

| 3,948,814 A | * | 4/1976 | de Rijke ...................... 512/25 |
|---|---|---|---|
| 4,448,712 A | * | 5/1984 | van der Weerdt et al. ...... 512/9 |
| 4,622,172 A |   | 11/1986 | Schreiber et al. |
| 5,698,253 A | * | 12/1997 | Dekker et al. .............. 426/538 |
| 5,888,961 A | * | 3/1999 | Rossiter ....................... 512/12 |

FOREIGN PATENT DOCUMENTS

| EP | 0 074 693 | 3/1983 |
|---|---|---|
| EP | 0 320 625 | 6/1989 |
| EP | 0 565 783 | 10/1993 |
| GB | 1 371 727 | 10/1974 |
| WO | WO 94/13766 | 6/1994 |
| WO | WO 96/30359 | 10/1996 |
| WO | WO 96/30469 | 10/1996 |

* cited by examiner

Primary Examiner—Jill Warden
Assistant Examiner—Monique T. Cole
(74) Attorney, Agent, or Firm—Morgan, Lewis & Bockius LLP

(57) ABSTRACT

A fragrance composition comprising a mixture of at least two of the following:

5-methyl-2-(2-methylpropyl-1,3-dioxane (Camonal);

methyl 1,4-dimethylcyclohexylcarboxylate (Cyprisate);

3-(((1-ethoxy)ethyl)oxy)-3,7-dimetyl-1,6-octadiene (Elintaal); and 7,9-dimethylspiro(5,5)undcan-3-one (Dispirone)

and use thereof to provide enhanced malodour reduction.

8 Claims, No Drawings

REDUCTION OF MALODOUR

This application is the National Phase of International Application PCT/GB99/04278 filed Dec. 16, 1999 which designated the U.S. and that International Application was published under PCT Article 21(2) in English.

FIELD OF THE INVENTION

This invention relates to reduction of malodour and concerns methods and compositions for reducing malodour.

BACKGROUND TO THE INVENTION

It is clearly desirable to be able to reduce malodours in many circumstances, eg in domestic environments where common malodours include kitchen malodour, bathroom (lavatory) malodours, and malodours in carpets and furnishings eg caused by pets. Other common types of malodour include body malodour and malodours on clothes, eg caused by perspiration, smoke, environmental odours etc. The term "malodour" is used to refer to smells or odours generally regarded as undesirable or unpleasant in nature.

It is well known to incorporate fragrance or perfume materials in a wide range of products such as kitchen and bathroom cleaning products, air fresheners, carpet and fabric cleaners, laundry products, personal hygiene products etc, with a view to reducing such malodours. See, for example, WO 97/07778 and EP 0780132.

The present invention is based on the surprising discovery that certain known perfume or fragrance materials, when used in admixture with one or more other perfume or fragrance materials, have a greater effect in reducing malodours than would be expected or predicted based on the effect in reducing malodours of the materials on their own, thus indicating the presence of a synergistic effect.

The perfume or fragrance materials concerned are as follows:
1. 5-methyl-2-(2-methylpropyl)-1,3-dioxane, which is described in WO 96/30359, and which will be referred to herein as "Camonal" or "Cam" for brevity.
2. Methyl 1,4-dimethylcyclohexylcarboxylate, which is described in EP 0673408, and which will be referred to herein as "Cyprisate" or "Cy" for brevity.
3. 3-(((1-ethyloxy)ethyl)oxy)-3,7-dimethyl-1,6-octadiene, which is described in GB 1371727, and which will be referred to herein as "Elintaal" or "El" for brevity.
4. 7,9-dimethylspiro(5,5)undecan-3-one, which is described in EP 0074693, and which will be referred to herein as "Dispirone" or "Dis" for brevity.

While these 4 materials are known to have attractive fragrance properties, their beneficial effect, when in admixture with other fragrance materials, in reducing malodours is not known and is not predictable.

SUMMARY OF THE INVENTION

In one aspect the present invention provides a fragrance composition comprising a mixture of two or more fragrance materials, including one or more of the following materials at least at the following minimum amounts by weight:
1. 5-methyl-2-(2-methylpropyl)-1,3-dioxane (Camonal) in an amount of at least 0.25%;
2. methyl 1,4-dimethylcyclohexylcarboxylate (Cyprisate) in an amount of at least 0.5%;
3. 3-(((1-ethyloxy)ethyl)oxy)-3,7-dimethyl-1,6-octadiene (Elintaal) in an amount of at least 15%; and
4. 7,9-dimethylspiro(5,5)undecan-3-one (Dispirone) in an amount of at least 2.5%.

In this specification, all references to % are % by weight unless otherwise specified.

The fragrance composition preferably includes at least two of the specified materials, preferably at least at the specified minimum amounts.

Camonal is preferably present at an amount of at least 7.5%. Cyprisate is preferably present in an amount in the range 0.5 to 15%. Elintaal is preferably present in an amount in the range 15 to 30%. Dispirone is preferably present in an amount of at least 2.5%.

There is a hedonic advantage in using mixtures as this allows a wider variety in fragrance hedonics to be produced with the same performance levels.

Mixtures containing 1:1:1 ratios of three of the ingredients perform well in all combinations. Mixtures containing 1:1 ratios of the ingredients should preferably contain Camonal or Cyprisate for good performance. Mixtures containing 1:1 ratios of Dispirone with an other ingredient should be avoided unless Camonal is used. Mixtures containing 2:1 ratios of ingredients perform best with either Canonal or Cyprisate at the highest proportion ingredient.

The terms "fragrance" and "perfume" are used synonymously in the present specification.

The terms "fragrance material" or "perfume material" are used herein to refer to a material which is added to a perfume or fragrance composition to contribute to the olfactive properties of the composition material. Typically, a perfume material will be generally recognised as possessing odours in its own right, will be relatively volatile and often has a molecular weight within the range 100 to 300. Typical perfume materials are described in "Perfume and Flavour Chemicals", Volumes I and II (Steffan Arctander, 1969).

The terms "perfume composition" or "fragrance composition" are used herein to mean a mixture of fragrance materials, if desired mixed with or dissolved in a suitable solvent or mixed with a solid substrate. The mixture may be a complex mixture of many ingredients. The composition may be used to impart a desired odour to the skin and/or any product for which an agreeable odour is indispensable or desirable. Examples of such products are: fabric washing powders, washing liquids, fabric softeners and other fabric care products; detergents and household cleaning, scouring and disinfection products; air fresheners, room sprays and pomanders; soaps, bath and shower gels, shampoos, hair conditioners and other personal cleansing products; cosmetics such as creams, ointments, toilet waters, preshave, aftershave, skin and other lotions, talcum powders, body deodorants and antiperspirants, etc.

Other fragrance materials which can advantageously be employed in the fragrance composition according to the invention are, for example, natural products such as extracts, essential oils, absolutes, resinoids, resins, concretes etc., but also synthetic materials such as hydrocarbons, alcohols, aldehydes, ketones, ethers, acids, esters, acetals, ketals, nitrites, etc., including saturated and unsaturated compounds, aliphatic, carbocyclic and heterocyclic compounds.

Such fragrance materials are mentioned, for example, in S. Arctander, Perfume and Flavor Chemicals (Montclair, N.J., 1969) in S. Arctander, Perfume and Flavor Materials of Natural Origin (Elizabeth, N.J., 1960) and in "Flavor and Fragrance, Materials—1991", Allured Publishing Co. Wheaton, Ill. USA.

It is preferred that other fragrance materials used in the fragrance composition of the invention are themselves not particularly good at reducing malodour but have medium, neutral or poor performance in this regard. The presence of one or more of Camonal, Cyprisate, Elintaal and Dispirone in the composition improves the malodour reduction properties of the composition.

Examples of fragrance materials which can be used in fragrance compositions to the invention are: geraniol, geranyl acetate, linalol, linalyl acetate, tetrahydrolinalol, citronellol, citronellyl acetate, dihydromyrcenol, dihydromyrcenyl acetate, tetrahydro-myrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzyl-carbinol, trichloromethylphenyl-carbinyl acetate, p-tert-butylcyclohexyl acetate, isononyl acetate, vetiveryl acetate, vetiverol, α-hexylcinnamaldehyde, 2-methyl-3-(p-tert-butylphenyl) propanal, 2-methyl-3-(p-isopropyl-phenyl)propanal, 3-(p-tert-butylphenyl)-propanal, 2,4-dimethylcyclohex-3-enyl-carboxaldehyde, tricyclodecenyl acetate, tricyclodecenyl propionate, 4-(4-hydroxy4-methylpentyl)-3-cyclohexenecarboxaldehyde, 4-(4-methyl-3-pentenyl)-3-cyclohexenecarboxyaldehyde, 4-acetoxy-3-pentyltetrahydropyran, 3-carboxymethyl-2-pentyl-cyclopentane, 2-n-heptylcyclopentanone, 3-methyl-2-pentyl-2-cyclopentenone, n-decanal, n-dodecanal, 9-decenol-1, phenoxyethyl isobutyrate, phenyl-acetaldehyde dimethyl-acetal, phenylacetaldehyde diethylacetal, geranyl nitrile, citronellyl nitrile, cedryl acetate, 3-isocamphyl-cyclohexanol, cedryl methyl ether, isolongifolanone, aubepine nitrile, aubepine, heliotropin, coumarin, eugenol, vanillin, diphenyl oxide, hydroxycitronellal, ionones, methylionones, isomethylionones, irones, cis-3-hexenol and esters thereof, indan musks tetralin musks isochroman musks macrocyclin ketones, macrolactone musks, ethylene brassylate.

Solvents which can be used for fragrance compositions according to the invention are, for example: ethanol, isopropanol, diethyleneglycol monoethyl ether, dipropylene glycol, diethyl phthalate, triethyl citrate, isopropyl myristate, etc.

The fragrance composition may be in the form of a fragrance base, that is typically a mixture of many fragrance materials (up to, say, 50) intended to be mixed in use with a neutral complex fragrance. The resulting mixture also constitutes a fragrance composition in accordance with the invention, and may be intended to be used either as a fragrance in its own right or to impart desirable fragrance (and malodour reduction properties) to a product, typically a consumer product, eg as discussed above.

The present invention therefore also provides a product comprising a fragrance composition in accordance with the invention.

The fragrance composition is used in the product at a suitable level depending on the product, to achieve the desired effect in terms of fragrance and malodour reduction properties of the product, with typical levels being in the range 0.1 to 10% by weight.

In a further aspect, the invention also provides use of Camonal, Cyprisate, Elintaal and/or Dispirone in a perfume composition for enhancing the malodour reduction properties of the composition.

The invention also includes within its scope a method of enhancing the malodour reduction properties of a fragrance composition, comprising including in the composition at least one of Camonal, Cyprisate, Elintaal and Dispirone.

The present invention is concerned particularly with reduction of malodour (ie reducing the perceived intensity of a malodour) not by masking the malodour (eg dominating the malodour with a stronger odour) but by counteracting or neutralising the malodour in a way that reduces perceived malodour intensity without the need for an intense perfume, or a perfume with a pronounced idiosyncratic odour character such as eucalyptus or wintergreen: this is thought to involve some sort of blocking interaction, possibly between the chemical reagents involved, or in the nose or brain of a subject, although the mechanism is not understood.

The performance of materials in reducing malodour was measured experimentally by assessing materials on their own and in mixtures for their effectiveness in reducing (counteracting) standard malodours in small scale headspace assessments carried out by trained sensory assessors. Tests were preferably carried out using fragrance materials at similar intensity levels, ie at levels subjectively assessed by the trained assessors to have similar perceived levels of fragrance intensity (referred to herein as iso-intense fragrance levels), rather than using materials necessarily at the same amounts by weight, so that reduction in malodour is more likely to be due to malodour counteraction (either by chemical or sensory mechanisms) than to malodour masking (by a fragrance material of stronger intensity).

DETAILED DESCRIPTION OF THE INVENTION

The invention will be further described, by way of illustration, in the following Examples.

Experimental Testing Procedure

Techniques have been developed for the accurate measurement of the performance of fragrance materials and compositions against standard malodours utilising small scale headspace assessments carried out by a sensory panel of trained sensory assessors.

The Sensory Panel

The sensory panel consists of a pool of between 25 and 35 members, who are all screened and then trained over a period of 6 months. Training includes learning to identify individual odour characters in complex mixtures, and to score their perceived intensity using a ratio scoring technique (Magnitude Estimation). The level of efficiency of the panel is continuously monitored to ensure a high level of accuracy and reproducibility.

Testing Environment

During testing all variables other than those actually under test are controlled as carefully as possible. Samples are always prepared so that they are, as far as possible, identical apart from their differences in odour. When presented to panellists they are presented in random order and given random 3-figure codes. A minimum of 28 assessments were collated for each sample.

All assessments reported in the examples were carried out in a purpose built panel suite. The suite is designed so that all external distractions (ie. odour, noise, movement) are eliminated, and the panellists are not distracted during testing.

Sample Preparation

The perfume material and malodour are placed alongside each other in a 500 ml glass vessel: 3 ml of malodour in a squat 15 ml jar alongside a perfume material (1 ml in a 15 ml upright jar). The vessel is closed and allowed to equilibrate for half an hour before assessment.

The Malodour

The malodours are selected for practical usefulness. Standard malodours have been identified which would be suitable. In these examples a bathroom malodour was used.

Sensory Assessment

Each panel member assesses each sample for the intensity of malodour and perfume material that can be perceived in the headspace of the glass vessel. Hidden blanks (malodour but no perfume) are included as internal controls. The scores for each of the panellists are normalised and averaged to give a consensus score across the whole panel.

Standard statistical techniques are employed to compare the performance of each perfume material against the malodour and the statistical significance of any differences detected. A performance value for each ingredient when tested in mixtures was calculated using the general linear models procedure (PROC REG) of the Statistical Analysis System (SAS). The SAS system is an integrated system of software developed by the SAS Institute Inc, SAS Campus Drive, Cary, N.C. 27514,USA. SAS is a registered Trade Mark. The REG procedure is a general purpose procedure fitting linear regression models by the method of least squares.

EXAMPLE 1

Single Ingredient Testing

In preliminary experiments various materials, including Camonal, Cyprisate, Elintaal and Dispirone, were tested singly and in various mixtures against the standard bathroom malodour. The materials other than Camonal, Cyprisate, Elintaal and Dispirone were included for comparative purposes.

Each ingredient was diluted with diethylphthalate (DEP) to a concentration which gave a fragrance intensity assessed by the panellists as similar to that of the intensity of a 0.5% dilution of standard bathroom malodour. The use of similar intensity fragrance levels reduces the risk of any occurrence of masking of malodour by the fragrance. Any reduction of malodour found is therefore likely to arise from malodour counteraction, by either chemical or sensory mechanisms.

Fragrance materials tested were as follows:

|  | Concentration in DEP |
| --- | --- |
| Elintaal | 100% |
| Cyprisate | 50% |
| Camonal | 25% |
| Dispirone | 50% |
| Animalis | 10% |
| Damascone alpha | 60% |
| Hexyl cinnamic aldehyde | 100% |
| Dimethyl hydroquinone | 50% |

All the ingredients tested in the. protocol described above gave malodour intensity scores in the range 30 to 59 (on a scale of 0 to 100), and so were classified as medium malodour couteractants as single ingredients.

The results of the fragrance materials tested are as follows:

| Ingredient | Malodour Score | Classification |
| --- | --- | --- |
| Elintaal | 45.0 | Medium |
| Cyprisate | 51.4 | Medium |
| Camonal | 36.6 | Medium |
| Dispirone | 33.4 | Medium |
| Animalis | 32.0 | Medium |
| Damascone alpha | 34.2 | Medium |
| Hexyl cinnamic aldehyde | 36.0 | Medium |
| Dimethyl hydroquinone | 30.0 | Medium |

The results show reduction of malodour from 70% to 49% by the ingredients. These ingredients therefore have some ability to reduce malodour as individual chemicals, but are not as good as some known materials. On this basis, these materials have been arbitrarily classed as having medium malodour reduction ability.

Mixture Testing

Each of the ingredients were also tested in 6 component mixes. The mixes were used to simulate possible inter-ingredient interactions caused by mixing into complex formulations. The ingredients were diluted to iso-intense levels prior to mixing. Each ingredient was incorporated into at least 6 different mixtures. Each mixture contained equal weight to weight ratios of the 6 iso-intense ingredients.

The mixtures were tested using the same testing procedure described above.

Parameter estimates were calculated using the PROC REG procedure in the SAS system. This is a general-purpose procedure fitting linear regression models by least squares. The parameter estimates for each ingredient in the mixtures were adjusted according to the concentration of the ingredient in the mixtures, and were then added together along with the calculated intercept. This gave predicted performance values for the single fragrance materials when incorporated into mixtures.

Results

The predicted values (predicted malodour score in the table below) obtained for the fragrance ingredients fell on a scale of −60 to +40. This slight change of scale occurs as a result of the statistical procedure followed. The results can be classified as shown below:

| Group 1: | Good malodour counteractants in mixtures | −60 to 0 |
| Group 2: | Medium malodour counteractants in mixtures | 0 to 40 |
| Group 3: | Poor malodour counteractants in mixtures | >40 |

The results for the fragrance materials tested are as follows:

| Ingredient | Predicted malodour score | Classification |
| --- | --- | --- |
| Elintaal | −16.8 | Good |
| Cyprisate | −27.8 | Good |
| Camonal | −50.0 | Good |
| Dispirone | −1.4 | Good |
| Animalis | 61.0 | Poor |
| Damascone alpha | 62.8 | Poor |
| Hexyl cinnamic aldehyde | 57.4 | Poor |
| Dimethyl hydroquinon | 68.8 | Poor |

The results show that the top 4 ingredients perform surprisingly well in mixtures, better than would have been expected from their single ingredients scores.

This surprising action of the ingredients unexpectedly enhances the performance of the mixtures in which they were tested. This unexpected action is as a result of synergism. This effect applies to Elintaal, Cyprisate, Carnonal and Dispirone only, and not the other materials tested in this experiment.

Confirmation of Synergistic Action

The four synergistic materials, Elintaal, Cyprisate, Camonal and Dispirone, were diluted to iso-intense levels and then mixed together in equal weight to weight ratios to form a simple synergistic base. This base was dosed into a neutral fragrance referred to as Chester, the formulation of which is given below, at a range of levels. The resulting mixes were tested against malodour using the method detailed previously.

Formulation of Neutral fragrance Chester:

| Ingredient | wt % |
| --- | --- |
| Benzyl salicylate | 5 |
| Cinnamic alcohol | 0.25 |
| DEP | 50 |
| Dihydromyrcenol | 5 |
| Diphenyl oxide | 2.5 |
| Heliotropin | 1 |
| Hydroxycitronellal | 5 |
| Indole | 0.1 |
| Lily aldehyde | 5 |
| Linalol | 5 |
| Lixetone | 2.5 |
| Methyl anthranilate | 0.5 |
| Methyl ionone alpha iso | 1.5 |
| Terpineol | 16.6 |
| Vanilin | 0.05 |

The results are shown below

| Malodour Intensity | Sample | | Fragrance Intensity | Sample | |
| --- | --- | --- | --- | --- | --- |
| 10 | Chester + 50% syn mix | a | 86 | Chester + 30% syn mix | a |
| 11 | Chester + 40% syn mix | a | 83 | Chester + 40% syn mix | a |
| 17 | Chester + 30% syn mix | a | 79 | Chester + 50% syn mix | a |
| 20 | Chester + 20% syn mix | b | 76 | Chester + 20% syn mix | b |
| 30 | Chester | b | 67 | Chester | b |
| 100 | Malodour only | | 0 | Malodour only | |

Please note: The samples with the same character (a or b) alongside are NOT significantly mix, different.

The results show that dosing in to Chester of 30% or more of the synergistic mix, significantly improves the performance of the neutral fragrance against bathroom malodour.

EXAMPLE 2

In further experiments, further similar tests were carried out using Camonal, Cyprisate, Dispirone and Elintaal singly at different concentrations and for different combinations of the 4 ingredients. The ingredients were tested dosed into Chester (which includes 50% DEP) against bathroom malodour.

Samples Tested

The four ingredients were diluted to iso-intense levels before dosing into Chester at the following levels.

| Single ingredients: | Camonal | 1%, 5%, 10%, 30% |
| --- | --- | --- |
| | Cyprisate | 1%, 5%, 10%, 30% |
| | Elintaal | 10%, 15%, 20%, 30% |
| | Dispirone | 5%, 10%, 20%, 30% |

Equal ratio mixtures of the following iso-intense ingredients dosed into Chester at 10%:

| 1:1 | Camonal:Elintaal |
| --- | --- |
| 1:1 | Camonal:Cyprisate |
| 1:1 | Camonal:Dispirone |
| 1:1 | Cyprisate:Elintaal |
| 1:1 | Cyprisate:Dispirone |
| 1:1 | Elintaal:Dispirone |
| 1:1:1 | Cyprisate:Camonal:Elintaal |
| 1:1:1 | Camonal:Elintaal:Dispirone |
| 1:1:1 | Cyprisate:Elintaal:Dispirone |
| 1:1:1 | Cyprisate:Camonal:Dispirone |
| 2:1 | Camonal:Cyprisate |
| 2:1 | Camonal:Elintaal |
| 2:1 | Camonal:Dispirone |
| 2:1 | Cyprisate:Elintaal |
| 2:1 | Cyprisate:Disprione |
| 2:1 | Elintaal:Camonal |
| 2:1 | Elintaal:Cyprisate |
| 2:1 | Dispirone:Elintaal |

NB: Iso-intense levels of the ingredients are shown as follows:

Camonal (25%)

Cyprisate (50%)

Dispirone (50%)

Elintaal (100%)

For purposes of clarification, Appendix 1 gives details of % of ingredients, DEP and fragrance used in the mixtures.

Method

A standard procedure described above was used. 1 ml of fragrance mixture was pipetted into 15 ml jars and placed into 500 ml vessels alongside 15 ml jars containing 3 ml of bathroom malodour at 0.5%. The vessels were sealed and allowed to come to equilibrium before assessment by a trained sensory panel using the technique of magnitude estimation.

Results

Testing of single ingredients dosed into Chester

Each of the four iso-intense ingredients was firstly tested dosed into Chester at 10% and 30%.

| Sample | | |
| --- | --- | --- |
| Malodour Intensity | | |
| 8 | Chester + 30% Camonal | abc |
| 12 | Chester + 10% Camonal | abcd |
| 13 | Chester + 10% Cyprisate | abcd |
| 13 | Chester + 30% Cyprisate | bcd |
| 18 | Chester + 10% Dispirone | bcde |
| 19 | Chester + 30% Elintaal | cde |
| 23 | Chester + 10% Elintaal | def |
| 26 | Chester + 30% Dispirone | efg |

-continued

| | Sample | |
|---|---|---|
| 35 | Chester | fg |
| 62 | Malodour only | |
| Fragrance Intensity | | |
| 89 | Chester + 30% Camonal | a |
| 82 | Chester + 30% Cyprisate | a |
| 79 | Chester + 10% Cyprisate | ab |
| 78 | Chester + 10% Camonal | abc |
| 66 | Chester + 10% Dispirone | bcd |
| 64 | Chester + 30% Elintaal | cd |
| 63 | Chester + 10% Elintaal | d |
| 57 | Chester + 30% Dispirone | de |
| 46 | Chester | e |
| 12 | Malodour only | |

Please note: The samples with the same character alongside are NOT significantly different.

The results show that:
1. Addition of either 10% or 30% of Camonal or Cyprisate has significantly improved the performance of Chester.
2. Addition of 30% of Elintaal has significantly improved the performance of Chester. A significant improvement is not seen with 10% of Elintaal.
3. Significant improvement of Chester is seen with 10% of Dispirone, but not with 30%. This maybe as a result of the unpleasant aspect of Dispirone odour when at higher concentration levels. This unpleasantness may be seen to add to the malodour intensity.

Following on from these results, Camonal and Cyprisate were tested again at lower dosage levels, Elintaal at levels between 10 and 30%, and Dispirone also at lower levels.

| | Sample | |
|---|---|---|
| Malodour Intensity | | |
| 4 | Chester + 10% Camonal | ab |
| 6 | Chester + 1% Cyprisate | ab |
| 6 | Chester + 10% Cyprisate | ab |
| 6 | Chester + 5% Camonal | ab |
| 9 | Chester + 15% Elintaal | abc |
| 10 | Chester + 5% Cyprisate | abc |
| 10 | Chester + 30% Elintaal | abc |
| 11 | Chester + 20% Elintaal | abc |
| 12 | Chester + 1% Camonal | bc |
| 20 | Chester + 5% Dispirone | cd |
| 24 | Chester + 10% Dispirone | de |
| 35 | Chester + 20% Dispirone | ef |
| 41 | Chester | f |
| 93 | Malodour only | |
| Fragrance Intensity | | |
| 102 | Chester + 10% Camonal | ab |
| 97 | Chester + 1% Cyprisate | abc |
| 94 | Chester + 5% Cyprisate | abc |
| 93 | Chester + 10% Cyprisate | abc |
| 93 | Chester + 5% Camonal | abc |
| 86 | Chester + 20% Elintaal | cd |
| 85 | Chester + 30% Elintaal | cd |
| 84 | Chester + 15% Elintaal | cd |
| 78 | Chester + 1% Camonal | de |
| 68 | Chester + 10% Dispirone | ef |
| 59 | Chester + 5% Dispirone | fg |
| 55 | Chester + 20% Dispirone | fg |
| 50 | Chester | g |
| 0 | Malodour only | |

Please note: The samples with the same character alongside are NOT significantly different.

The results show that:
1. For Camonal, there is no significant difference between dosing in 1%, 5% or 10%.
   As concentration increases there is a directional improvement in the fragrance performance.
2. For Cyprisate, there is no significant difference between dosing in 1%, 5% or 10%.
3. For Elintaal, there is no significant difference between dosing in 15%, 20% or 30%.
4. For Dispirone, dosing in 10% or 5% significantly improved the performance of improvement is not seen with 20% Dispirone.

| Testing of 1:1 and 1:1:1 mixes of ingredients dosed into Chester | | |
|---|---|---|
| | Sample | |
| Malodour Intensity | | |
| 4 | Chester + 1:1 Cam:El | ab |
| 7 | Chester + 1:1:1 Cy:Cam:El | ab |
| 7 | Chester + 1:1:1 Cam:El:Dis | ab |
| 8 | Chester + 1:1 Cy:Cam | ab |
| 11 | Chester + 1:1 Cam:Dis | ab |
| 12 | Chester + 30% Elintaal | ab |
| 13 | Chester + 10% Cyprisate | ab |
| 14 | Chester + 1:1:1 Cy:El:Dis | ab |
| 17 | Chester + 15% Camonal | b |
| 17 | Chester + 1:1:1 Cy:Cam:Dis | b |
| 17 | Chester + 1:1 Cy:El | b |
| 33 | Chester + 1:1 El:Dis | c |
| 35 | Chester + 1:1 Cy:Dis | c |
| 43 | Chester | c |
| 93 | Malodour only | |
| Fragrance Intensity | | |
| 90 | Chester + 1:1 Cam:El | bc |
| 81 | Chester + 1:1:1 Cy:Cam:El | cd |
| 81 | Chester + 30% Elintaal | cd |
| 80 | Chester + 1:1 Cy:Cam | cd |
| 79 | Chester + 1:1:1 Cam:El:Dis | cd |
| 77 | Chester + 10% Cyprisate | cd |
| 76 | Chester + 15% Camonal | cd |
| 76 | Chester + 1:1 Cam:Dis | cd |
| 73 | Chester + 1:1 Cy:El | d |
| 71 | Chester + 1:1:1 Cy:El:Dis | de |
| 65 | Chester + 1:1:1 Cy:Cam:Dis | def |
| 56 | Chester + 1:1 Cy:Dis | efg |
| 48 | Chester | fg |
| 46 | Chester + 1:1 El:Dis | g |
| 0 | Malodour only | |

Please note: The samples with the same character alongside are NOT significantly different.

The results show that:
1. Of the mixtures tested, all performed significantly better than Chester except 1:1 Elintaal Dispirone and 1:1 Cyprisate:Dispirone.
2. There were no significant differences seen between the good performing mixtures.
3. Directional differences were seen in the results which can be summarised as follows:

Mixtures containing Camonal and Elintaal performed best

1:1 mixtures containing Dispirone performed badly except when Camonal was the other ingredient.

1:1:1 mixtures all performed well even if they contained Dispirone

1:1 mixtures containing Cyprisate performed well except with Dispirone.

Testing of 2:1 mixtures of ingredients dosed into Chester

| Sample | | |
|---|---|---|
| Malodour Intensity | | |
| 4 | Chester + 2:1 Cam:Cy | abcd |
| 5 | Chester + 2:1 Cam:El | abcd |
| 10 | Chester + 2:1 Cy:Cam | abcde |
| 11 | Chester + 2:1 Cy:El | abcde |
| 17 | Chester + 2:1 Cy:Dis | bcde |
| 18 | Chester + 2:1 Cam:Dis | cde |
| 21 | Chester + 2:1 El:Cam | de |
| 22 | Chester + 2:1 El:Cy | e |
| 42 | Chester | f |
| 44 | Chester + 2:1 Dis:El | f |
| 79 | Malodour only | |
| Fragrance Intensity | | |
| 86 | Chester + 2:1 Cam:El | a |
| 85 | Chester + 2:1 Cam:Cy | a |
| 80 | Chester + 2:1 Cy:Cam | ab |
| 78 | Chester + 2:1 Cam:Dis | ab |
| 77 | Chester + 2:1 Cy:El | abc |
| 66 | Chester + 2:1 Cy:Dis | bcd |
| 59 | Chester + 2:1 El:Cam | cd |
| 57 | Chester + 2:1 El:Cy | d |
| 39 | Chester + 2:1 Dis:El | e |
| 35 | Chester | e |
| 2 | Malodour only | |

Please note: The samples with the same character alongside are NOT significantly different.

The results show that:
1. Of the mixtures tested, all performed significantly better than Chester except 2:1 Dispirone Elintaal.
2. There are few significant differences seen between the good performing mixes.
3. Directional differences were seen in results which can be summarised as follows:

Mixtures with Cyprisate or Carnonal in the greatest proportion performed best.

The 2:1 Camonal:Cyprisate performed better than 2:1 Cyprisate:Camonal

While the synergistic ingredients can be used at any level, the following provides recommendations for levels which can lead to significant synergistic benefit.

Use of the four ingredients are as follows. All recommendations refer to use of ingredients at iso-intense levels.

Singly:
Preferably use as follows:
Camonal—use at 1% or more. The higher the concentration the better the effect directionally.
Cyprisate—use at 1% or more. Concentration does not seem to affect performance.
Elintaal—use at 15% or more. Concentration above 15% does not seem to affect performance.
Dispirone—use at 5%–10%. Use of more than 10% adds to the malodour perception. due to the unpleasant smell of Dispirone at high levels.

Mixtures:
While no performance advantage is seen using mixtures of the four ingredients opposed to use singly, there is, however, a hedonic advantage in using mixtures as this allows a wider variety in fragrance hedonics to be produced with the same performance levels.

Mixtures containing 1:1:1 ratios of three of the ingredients perform well in all combinations.

Mixtures containing 1:1 ratios of the ingredients must contain Camonal or Cyprisate for good performance.

Mixtures containing 1:1 ratios of Dispirone with an other ingredient should be avoided unless Camonal is used.

Mixtures containing 2:1 ratios of ingredients perform best with either Camonal or Cyprisate as the highest proportion ingredient.

Appendix 1
% for Single dosing-in mixtures:

| Mixture | % Ingredient | % DEP | % Fragrance |
|---|---|---|---|
| Chester + 1% Camonal | 0.25 | 0.75 | 99 |
| Chester + 5% Camonal | 1 | 4 | 95 |
| Chester + 10% Camonal | 2.5 | 7.5 | 90 |
| Chester + 30% Camonal | 7.5 | 22.5 | 70 |
| Chester + 1% Cyprisate | 0.5 | 0.5 | 99 |
| Chester + 5% Cyprisate | 2.5 | 2.5 | 95 |
| Chester + 10% Cyprisate | 5 | 5 | 90 |
| Chester + 30% Cyprisate | 15 | 15 | 70 |
| Chester + 10% Elintaal | 10 | 0 | 90 |
| Chester + 15% Elintaal | 15 | 0 | 85 |
| Chester + 20% Elintaal | 20 | 0 | 80 |
| Chester + 30% Elintaal | 30 | 0 | 70 |
| Chester + 5% Dispirone | 2.5 | 2.5 | 95 |
| Chester + 10% Dispirone | 5 | 5 | 90 |
| Chester + 20% Dispirone | 10 | 10 | 80 |
| Chester + 30% Dispirone | 15 | 15 | 70 |

% for 1:1 mixtures

| Mixture | % first ingredient | % second ingredient | % DEP | % Fragrance |
|---|---|---|---|---|
| Chester + 1:1 Cam:El | 1 | 5 | 4 | 90 |
| Chester + 1:1 Cam:Cy | 1 | 2.5 | 6.5 | 90 |
| Chester + 1:1 Cam:Dis | 1 | 2.5 | 6.5 | 90 |
| Chester + 1:1 Cy:El | 2.5 | 5 | 2.5 | 90 |
| Chester + 1:1 Cy:Dis | 2.5 | 2.5 | 5 | 90 |
| Chester + 1:1 El:Dis | 5 | 2.5 | 2.5 | 90 |

% for 1:1:1 mixtures

| Mixture | % first ingredient | % second ingredient | % third ingredient | % DEP | % Fragrance |
|---|---|---|---|---|---|
| Chester + Cy:Cam:El | 1.67 | 0.83 | 3.33 | 4.14 | 90 |
| Chester + Cam:El:Dis | 0.83 | 3.33 | 1.67 | 4.14 | 90 |
| Chester + Cy:El:Dis | 1.67 | 3.33 | 1.67 | 3.33 | 90 |
| Chester + Cy:Cam:Dis | 1.67 | 0.83 | 1.67 | 5.83 | 90 |

% for 2:1 mixtures

| Mixture | % main ingredient | % secondary ingredient | % DEP | % Fragrance |
|---|---|---|---|---|
| Chester + 2:1 Cam:Cy | 1.66 | 1.67 | 6.66 | 90 |
| Chester + 2:1 Cam:El | 1.66 | 3.33 | 5.01 | 90 |
| Chester + 2:1 Cam:Dis | 1.66 | 1.67 | 6.66 | 90 |
| Chester + 2:1 Cy:El | 3.33 | 3.33 | 3.33 | 90 |
| Chester + 2:1 Cy:Dis | 3.33 | 1.67 | 5.00 | 90 |
| Chester + 2:1 El:Cam | 6.66 | 0.83 | 7.49 | 90 |
| Chester + 2:1 El:Cy | 6.66 | 1.67 | 8.33 | 90 |
| Chester + 2:1 Dis:El | 3.33 | 6.66 | 9.96 | 90 |

What is claimed is:

1. A fragrance composition characterized by its enhanced malodour reduction properties comprising a synergistically effective mixture of two or more fragrance materials selected from the group consisting of:
   1. 5-methyl-2-(2-methylpropyl-1,3-dioxane (Camonal);
   2. methyl 1,4-dimethylcyclohexylcarboxylate (Cyprisate);
   3. 3-(((1-ethoxy)ethyl)oxy)-3,7-dimetyl-1,6-octadiene (Elintaal); and
   4. 7,9-dimethylspiro(5,5)undcan-3-one (Dispirone) said mixture being present in amount sufficient to provide enhanced reduction of malodour with the provisos that if the composition contains only two fragrance materials, either Camonal or Cyprisate is present; and if the composition contains only two fragrance materials with one fragrance material being Dispirone, the other fragrance material is Camonal.

2. A composition according to claim 1 wherein the materials when present are at least at the following minimum amounts by weight:
   1. Camonal in an amount of at least 0.25%;
   2. Cyprisate in an amount of at least 0.5%;
   3. Elintaal in an amount of at least 15%; and
   4. Dispirone in an amount of at least 2.5%.

3. A composition according to claim 2, wherein the materials when present are at the following amounts by weight: Camonal at least 7.5%, Cyprisate in the range 0.5 to 15%, Elintaal in the range 15 to 30% and Dispirone at least 2.5%.

4. A composition according to claim 2, including one or more further fragrance materials having medium, neutral or poor malodour reduction properties.

5. A composition according to claim 2, comprising a fragrance base.

6. A product comprising a composition in accordance with claim 2.

7. A method of obtaining enhanced malodour reduction which comprises applying to a situs requiring such reduction a perfume composition including a mixture of at least two members of the group consisting of Camonal, Cyprisate, Elintaal and Dispirone, said mixture being synergistically effective in the reduction of malodours with the provisos that if the composition contains only two fragrance materials, either Camonal or Cyprisate is present; and if the composition contains only two fragrance materials with one fragrance material being Dispirone, the other fragrance material is Camonal.

8. A method of enhancing the malodour reduction properties of a fragrance composition, comprising including in the composition at least two of Camonal, Cyprisate, Elintaal and Dispirone with the provisos that if the composition contains only two fragrance materials, either Camonal or Cyprisate is present; and if the composition contains only two fragrance materials with one fragrance material being Dispirone, the other fragrance material is Camonal.

* * * * *